(12) United States Patent
Constantin et al.

(10) Patent No.: US 11,951,284 B2
(45) Date of Patent: Apr. 9, 2024

(54) TRANSITIONING TO OTHER MODES IN AUTOMATED INSULIN DELIVERY

(71) Applicant: Tandem Diabetes Care, Inc., San Diego, CA (US)

(72) Inventors: Alexandra Elena Constantin, San Diego, CA (US); Michael Michaud, San Diego, CA (US); Geoffrey A. Kruse, San Diego, CA (US); Thomas R. Ulrich, Oceanside, CA (US); Paul Harris, San Diego, CA (US); Virginia S. Lu, San Diego, CA (US); Garrett Marin, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 160 days.

(21) Appl. No.: 17/459,129

(22) Filed: Aug. 27, 2021

(65) Prior Publication Data

US 2022/0062553 A1 Mar. 3, 2022

Related U.S. Application Data

(60) Provisional application No. 63/071,154, filed on Aug. 27, 2020.

(51) Int. Cl.
*A61M 5/172* (2006.01)
*G16H 20/17* (2018.01)

(52) U.S. Cl.
CPC .......... *A61M 5/1723* (2013.01); *G16H 20/17* (2018.01); *A61M 2205/3576* (2013.01); *A61M 2230/201* (2013.01)

(58) Field of Classification Search
CPC ........ A61M 5/1723; A61M 2205/3576; A61M 2230/201; A61M 2005/14208; A61M 5/14244; A61M 2205/50; G16H 20/17
See application file for complete search history.

(56) References Cited

U.S. PATENT DOCUMENTS

| 2,674,262 | A | 4/1954 | Bradshaw |
| 3,875,979 | A | 4/1975 | Hults |
| 3,985,133 | A | 10/1976 | Jenkins et al. |
| 4,776,842 | A | 10/1988 | Franetzki et al. |

(Continued)

*Primary Examiner* — Emily L Schmidt
*Assistant Examiner* — Nelson Louis Alvarado, Jr.
(74) *Attorney, Agent, or Firm* — MERCHANT & GOULD P.C.

(57) ABSTRACT

Apparatuses and methods for transitioning to sleep mode or otherwise modified glucose target range in automated insulin delivery systems. For example, sleep mode can include a lower glucose target and/or lower and narrower glucose target range because of fewer variables that affect glucose values during sleep such as eating and exercise. Due to increased stability provided by the sleep mode target range, it is desirable to transition to the sleep mode target range as quickly as possible, while ensuring the transition is done safely and does not risk low glucose or hypoglycemia by too quickly switching to the lower and narrower target range. Systems and methods disclosed herein therefore provide various approaches for safely and quickly transitioning to sleep mode or other modified target ranges in order to improve time in range by being more aggressive to get to the lower sleep mode or other target faster without risking hypoglycemia.

20 Claims, 7 Drawing Sheets

(56) References Cited

U.S. PATENT DOCUMENTS

| | | |
|---|---|---|
| 5,059,171 A | 10/1991 | Bridge et al. |
| 5,103,211 A | 4/1992 | Daoud et al. |
| 5,256,157 A | 10/1993 | Samiotes et al. |
| 5,482,446 A | 1/1996 | Williamson et al. |
| 5,569,186 A | 10/1996 | Lord et al. |
| 5,582,593 A | 12/1996 | Hultman |
| 5,897,530 A | 4/1999 | Jackson |
| 5,976,780 A | 11/1999 | Shah |
| 6,080,130 A | 6/2000 | Castellano |
| 6,164,924 A | 12/2000 | Gruett et al. |
| 6,245,347 B1 | 6/2001 | Zhang et al. |
| 6,302,855 B1 | 10/2001 | Lav et al. |
| 6,595,948 B2 | 7/2003 | Suzuki et al. |
| 6,620,130 B1 | 9/2003 | Ginsburg |
| 6,673,034 B2 | 1/2004 | Castellano |
| 6,770,054 B1 | 8/2004 | Smolyarov et al. |
| 6,942,006 B2 | 9/2005 | Kono |
| 6,979,315 B2 | 12/2005 | Rogers et al. |
| 7,311,693 B2 | 12/2007 | Shekalim |
| 7,476,209 B2 | 1/2009 | Gara et al. |
| 7,944,366 B2 | 5/2011 | Krulevitch et al. |
| 8,147,448 B2 | 4/2012 | Sundar et al. |
| 8,231,572 B2 | 7/2012 | Carter et al. |
| 8,273,052 B2 | 9/2012 | Damiano et al. |
| 8,282,625 B2 | 10/2012 | Ullestad et al. |
| 8,313,308 B2 | 11/2012 | Lawless et al. |
| 8,409,133 B2 | 4/2013 | Pesach et al. |
| 8,475,409 B2 | 7/2013 | Tsoukalis |
| 8,491,566 B2 | 7/2013 | Ramey et al. |
| 9,089,305 B2 | 7/2015 | Hovorka |
| 9,384,652 B2 | 7/2016 | Gilham et al. |
| 9,483,615 B2 | 11/2016 | Roberts |
| 9,486,171 B2 | 11/2016 | Saint |
| 9,757,510 B2 | 9/2017 | Finan |
| 10,016,561 B2 | 7/2018 | Saint et al. |
| 10,493,202 B2 | 12/2019 | Hayter |
| 10,549,036 B2 | 2/2020 | Starkweather et al. |
| 10,556,055 B2 | 2/2020 | Briggs |
| 10,610,640 B2 | 4/2020 | Gonnelli et al. |
| 10,850,033 B2 | 12/2020 | Kovelman |
| 10,856,786 B2 | 12/2020 | Steil et al. |
| 11,083,843 B2 | 8/2021 | Hayter et al. |
| 11,090,432 B2 | 8/2021 | DeBelser et al. |
| 11,471,598 B2 | 10/2022 | Estes |
| 11,707,567 B2 | 7/2023 | Kamen et al. |
| 2003/0208113 A1 | 11/2003 | Mault et al. |
| 2008/0228056 A1 | 9/2008 | Blomquist et al. |
| 2010/0274323 A1 | 10/2010 | Williamson et al. |
| 2015/0217052 A1* | 8/2015 | Keenan ............ G16H 20/17 604/504 |
| 2016/0030669 A1 | 2/2016 | Harris et al. |
| 2019/0388015 A1 | 12/2019 | Blomquist |
| 2020/0101226 A1 | 4/2020 | Rosinko et al. |
| 2020/0171249 A1 | 6/2020 | Rosinko |
| 2020/0179603 A1 | 6/2020 | Rosinko |
| 2020/0254174 A1 | 8/2020 | Kruse et al. |
| 2020/0368430 A1 | 11/2020 | Ulrich et al. |
| 2021/0001038 A1 | 1/2021 | Rosinko |
| 2021/0001044 A1 | 1/2021 | Michaud et al. |
| 2021/0012875 A1 | 1/2021 | Blomquist et al. |
| 2021/0012876 A1 | 1/2021 | Blomquist |
| 2021/0113766 A1 | 4/2021 | Kearns et al. |
| 2021/0154405 A1 | 5/2021 | Kearns et al. |
| 2021/0193288 A1 | 6/2021 | Blomquist |
| 2021/0402091 A1 | 12/2021 | Harris |
| 2022/0134001 A1 | 5/2022 | Ulrich et al. |
| 2023/0034283 A1 | 2/2023 | Michaud et al. |

\* cited by examiner

TRANSITIONING TO OTHER MODES IN AUTOMATED INSULIN DELIVERY

RELATED APPLICATION

This application claims the benefit of U.S. Provisional Application No. 63/071,154 filed Aug. 27, 2020, which is hereby fully incorporated herein by reference.

FIELD OF THE INVENTION

The present invention relates generally to ambulatory infusion pumps and, more particularly, to operation of ambulatory infusion pumps in a closed-loop or semi-closed-loop fashion.

BACKGROUND OF THE INVENTION

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type 1, or in some cases, type 2 diabetes. Some insulin injecting pumps are configured as portable or ambulatory infusion devices that can provide continuous subcutaneous insulin injection and/or infusion therapy as an alternative to multiple daily insulin injections via syringe or injector pen. Such ambulatory infusion pumps may be worn by the user, may use replaceable medicament cartridges, and may deliver other medicaments alone, or in combination with insulin. Such medicaments include glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as continuous glucose monitoring devices (CGMs). A CGM device consists of a sensor placed under the patient's skin and affixed to the patient via an adhesive patch, a transmitter, and a monitor. A CGM device samples the patient's interstitial fluid periodically (e.g., once every 1-5 minutes) to estimate blood glucose levels over time. CGMs are advantageous because they provide more frequent insights into a user's blood glucose levels yet do not require a finger stick each time a reading is taken.

Ambulatory infusion pumps may incorporate a CGM within the hardware of the pump or may communicate with a dedicated CGM directly via a wired connection or indirectly via a wireless connection using wireless data communication protocols to communicate with a separate device (e.g., a dedicated remote device or a smartphone). One example of integration of ambulatory infusion pumps with CGM devices is described in U.S. Patent Publication No. 2014/0276419, which is hereby incorporated by reference herein. Ambulatory infusion pumps typically allow the user or caregiver to adjust the amount of insulin or other medicament delivered by a basal rate or a bolus, based on blood glucose data obtained by a CGM device, and in some cases include the capability to automatically adjust such medicament delivery. For example, based on CGM readings, some ambulatory infusion pumps may automatically adjust or prompt the user to adjust the level of medicament being administered or planned for administration or, in cases of abnormally low blood glucose readings, reducing or temporarily ceasing insulin administration.

In some cases, ambulatory insulin pumps may be configured to deliver insulin based on CGM data in a closed-loop or semi-closed-loop fashion. Some systems including these features may be referred to as automated insulin delivery (AID) systems or artificial pancreas systems because the systems serve to mimic biological functions of the pancreas for patients with diabetes.

Some AID systems include a sleep mode that can be turned on when a user is sleeping that can include a more aggressive (i.e., lower and narrower) glucose target because there are fewer variables that affect glucose values during sleep such as eating and exercise. For example, in a system where the target range is 112.5 mg/dL to 160 mg/dL, the target range during sleep mode may be 110 mg/dL to 120 mg/dL. In various systems, sleep mode can be activated manually and/or a user can set a stored sleep schedule. Systems typically gradually transition to the sleep mode target range in order to avoid the risk of hypoglycemia due to the lower and narrower target range. However, due to the increased stability provided by the sleep mode target range, it is desirable to transition to the sleep mode target range as quickly as can be safely done.

SUMMARY

Disclosed herein are apparatuses and methods for transitioning to a sleep mode or otherwise modified glucose target range in an automated insulin delivery system. For example, the sleep mode can include a lower glucose target and/or lower and narrower glucose target range because there are fewer variables that affect glucose values during sleep such as eating and exercise. Due to the increased stability provided by a sleep mode target range or otherwise modified target range, it is desirable to transition to the new target range as quickly as possible, while ensuring that the transition is done safely and does not risk low glucose or hypoglycemia by too quickly switching to the lower and narrower target range. Systems and methods disclosed herein therefore provide various approaches for safely and quickly transitioning to sleep mode or other modified target ranges in order to improve time in range by being more aggressive to get to the lower sleep mode or other target faster without risking hypoglycemia.

In embodiments, the system can base a speed at which the glucose target or target range transitions to sleep mode on a time since a most recent bolus was delivered to the user. If the most recent bolus was delivered greater than a predetermined amount of time prior to initiating sleep mode, the system can immediately transition directly to the sleep mode target. If the most recent bolus was delivered more recently than the predetermined amount of time, the system can instead gradually transition to the sleep mode target at a rate based on the amount of time since the most recent bolus. Such transitions can further be applied to additional modes and/or any other time that a target glucose level or range is modified.

In embodiments, the system can determine a transition to sleep mode algorithmically based on a probability of the user going below a low glucose threshold according to various factors. The factors can include patient-specific glucose level data and the probability of the user going low at a given time based on the data. For example, a mean glucose level and glucose variability can be tracked for a user based on time of day and retrospectively used to determine a probability of the user going below the low glucose threshold for any given period of time (e.g., each hour, each half hour etc.) over the course of a day. A patient-specific sleep schedule can be set based on the glucose level data. Such transitions can further be applied to additional modes and/or any other time that a target glucose level or range is modified.

In embodiments, the transition to sleep mode can be based on an estimated amount of insulin on board active in the patient's body. AID systems utilize a period of time, insulin action time (IAT), that insulin is estimated to remain active in the body, such as, for example, 5 hours. Therefore, utilizing the IAT estimate and the known history of insulin delivery the system, the system can estimate the user's IOB at any given time. The system can base its transition to the lower sleep mode target on this estimate of insulin on board because the more insulin that is active in the user's system, the greater the risk will drop below a low glucose threshold. Therefore, the system can delay or slow the transition to sleep mode until the estimated IOB for the user is below a predetermined threshold level. Such transitions can further be applied to additional modes and/or any other time that a target glucose level or range is modified.

In an embodiment, an ambulatory infusion pump system can include a pump mechanism configured to facilitate delivery of insulin to a user, a communications interface adapted to receive glucose levels from a continuous glucose monitor and at least one processor functionally linked to the pump mechanism and the communications interface. The at least one processor can be configured to automatically calculate insulin doses with a closed loop delivery algorithm based on glucose levels received from the continuous glucose monitor to maintain the user's glucose levels within a first target glucose range including a low glucose threshold and a high glucose threshold and to automatically deliver the insulin doses with the pump mechanism. If it is determined by the at least one processor that the first target glucose range should be modified from the first target glucose range to a second target glucose range, an amount of time elapsed since a most recent bolus delivery of insulin has been delivered by the pump mechanism can be determined. If the time period since the most recent bolus delivery of insulin is greater than a predetermined amount of time from the determination to modify the first target glucose range, the at least one processor can immediately transition from the first target glucose range to the second target glucose range. If the time period since the most recent bolus delivery of insulin is less than the predetermined amount of time from the determination to modify the first target glucose range, the at least one processor can gradually transition from the first target glucose range to the second target glucose range.

In an embodiment, an ambulatory infusion pump system can include a pump mechanism configured to facilitate delivery of insulin to a user, a communications interface adapted to receive glucose levels from a continuous glucose monitor and at least one processor functionally linked to the pump mechanism and the communications interface. The at least one processor can be configured to automatically calculate insulin doses with a closed loop delivery algorithm based on glucose levels received from the continuous glucose monitor to maintain the user's glucose levels within a first target glucose range including a low glucose threshold and a high glucose threshold and to automatically deliver the insulin doses with the pump mechanism. If it is determined by the at least one processor that the first target glucose range should be modified from the first target glucose range to a second target glucose range, an amount of time elapsed since a most recent bolus delivery of insulin has been delivered by the pump mechanism can be determined. The at least one processor can alter the first target glucose range to the second target glucose range if the time period since the last bolus is greater than a predetermined amount of time from the determination to modify the first target glucose range.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which.

Figure 1:
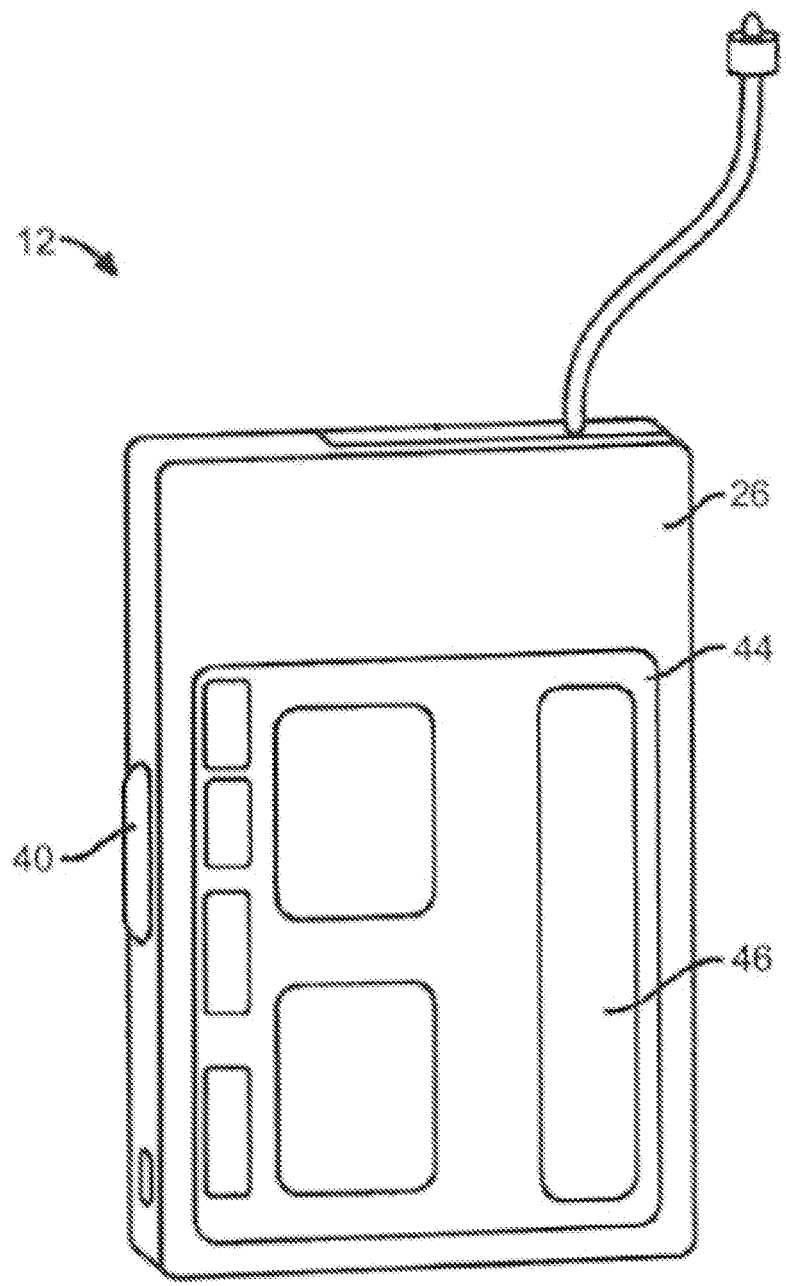
FIG. 1 is an embodiment of an ambulatory infusion pump for use with embodiments of the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an example infusion pump that can be used in conjunction with one or more embodiments of the ambulatory infusion pump system of the present disclosure. Pump 12 includes a pumping or delivery mechanism and reservoir for delivering insulin or other medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display (e.g., a dedicated remote display or a CGM display), a remote control device, or a consumer electronic device (e.g., laptop computer, personal computer, tablet computer, smartphone, electronic watch, electronic health or fitness monitor, or personal digital assistant). Further details regarding such pump devices can be found in U.S. Pat. No. 8,287,495, previously incorporated by reference above. It is to be appreciated that pump 12 may be optionally configured to deliver one or more additional or other medicaments to a patient.

Figure 2:
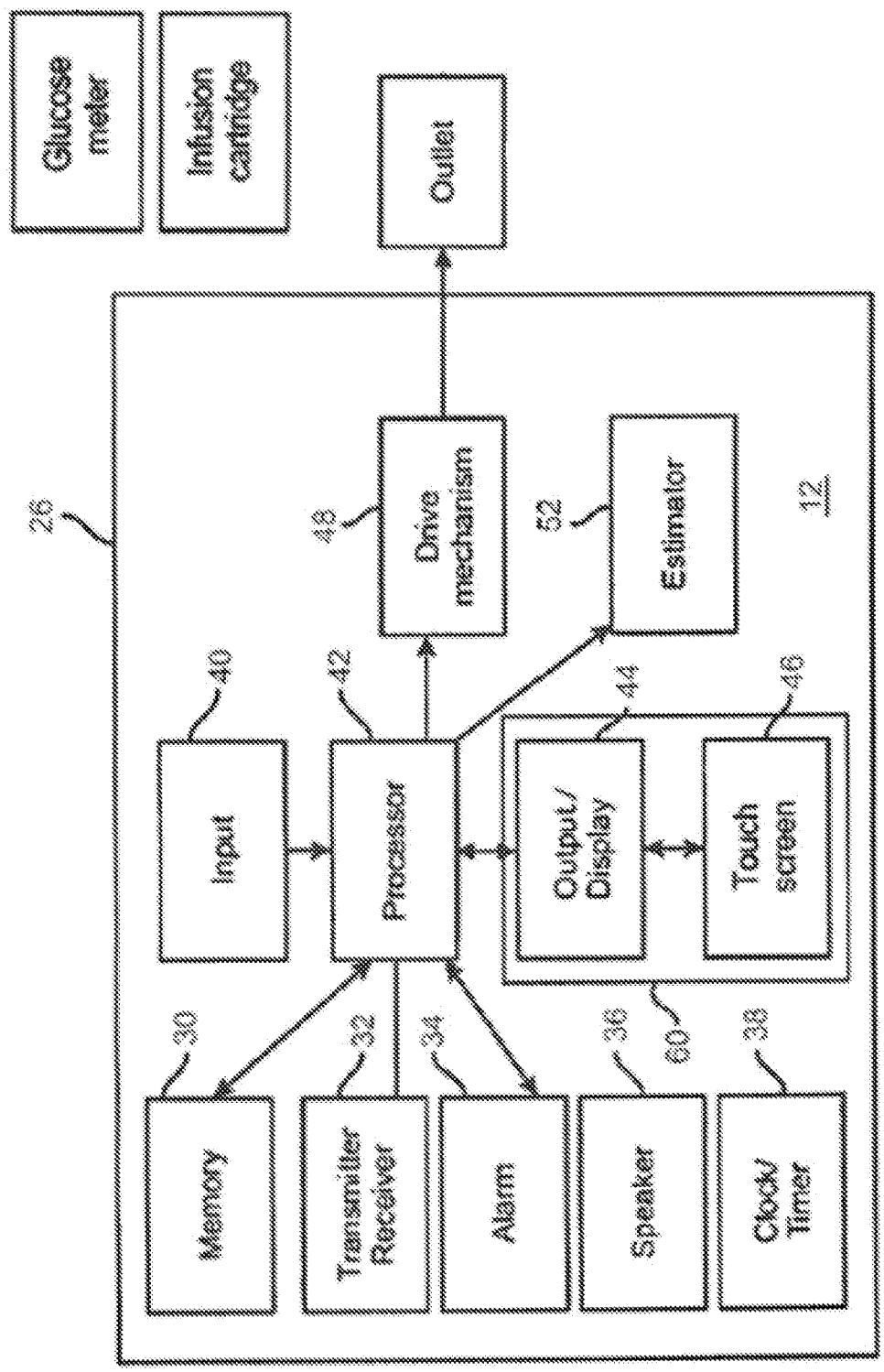
FIG. 2 is a block of the ambulatory infusion pump of FIG. 1.

FIG. 2 illustrates a block diagram of some of the features that may be included within the housing 26 of pump 12. The pump 12 can include a processor 42 that controls the overall functions of the pump. The pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices through the transmitter/receiver 32 such as a remote device (e.g., CGM device), a remote control device, or a consumer electronic device (e.g., laptop computer, personal computer, tablet computer, smartphone, electronic watch, electronic health or fitness monitor, or personal digital assistant). In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. The processor 42 may also include programming to receive signals and/or other data from an input device, such as, by way of example, a pressure sensor, a temperature sensor, or the like.

Figure 3A:
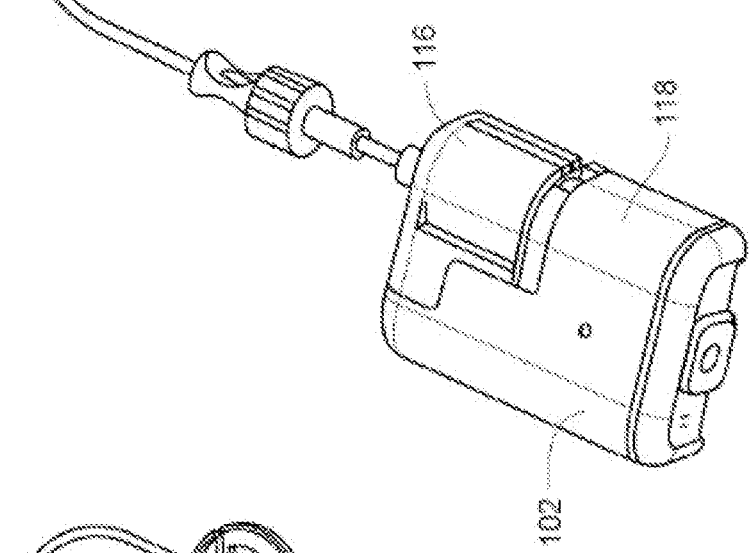
FIGS. 3A-3B are an alternate embodiment of an ambulatory infusion pump for use with embodiments of the disclosure.
Figure 3B:
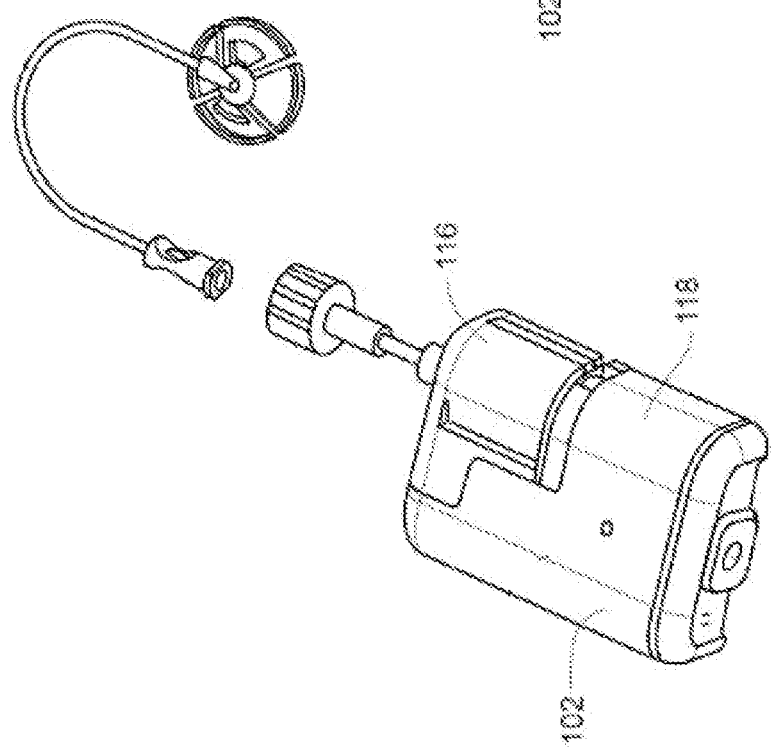

FIGS. 3A-3B depicts a second infusion pump that can be used in conjunction with one or more embodiments of the ambulatory infusion pump system of the present disclosure. Pump 102 includes a pump drive unit 118 and a medicament cartridge 116. Pump 102 includes a processor that may communicate with one or more processors within the pump 102 and/or one or more processors of other devices such as a remote device (e.g., a CGM device), a remote control device, or a consumer electronic device (e.g., laptop computer, personal computer, tablet computer, smartphone, electronic watch, electronic health or fitness monitor, or personal digital assistant). The processor 42 may also include programming to receive signals and/or other data from an input device, such as, by way of example, a pressure sensor, a temperature sensor, or the like. Pump 102 also includes a processor that controls some or all of the operations of the pump. In some embodiments, pump 102 receive commands from a separate device for control of some or all of the operations of the pump. Such separate device can include, for example, a dedicated remote control device or a consumer electronic device such as a smartphone executing an application configured to enable the device to transmit operating commands to the processor of pump 102. In some embodiments, processor can also transmit information to one or more separate devices, such as information pertaining to device parameters, alarms, reminders, pump status, etc. Such separate device can include any remote display, remote control device, or a consumer electronic device as described above. Pump 102 can also incorporate any or all of the features described with respect to pump 12 in FIG. 2. In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
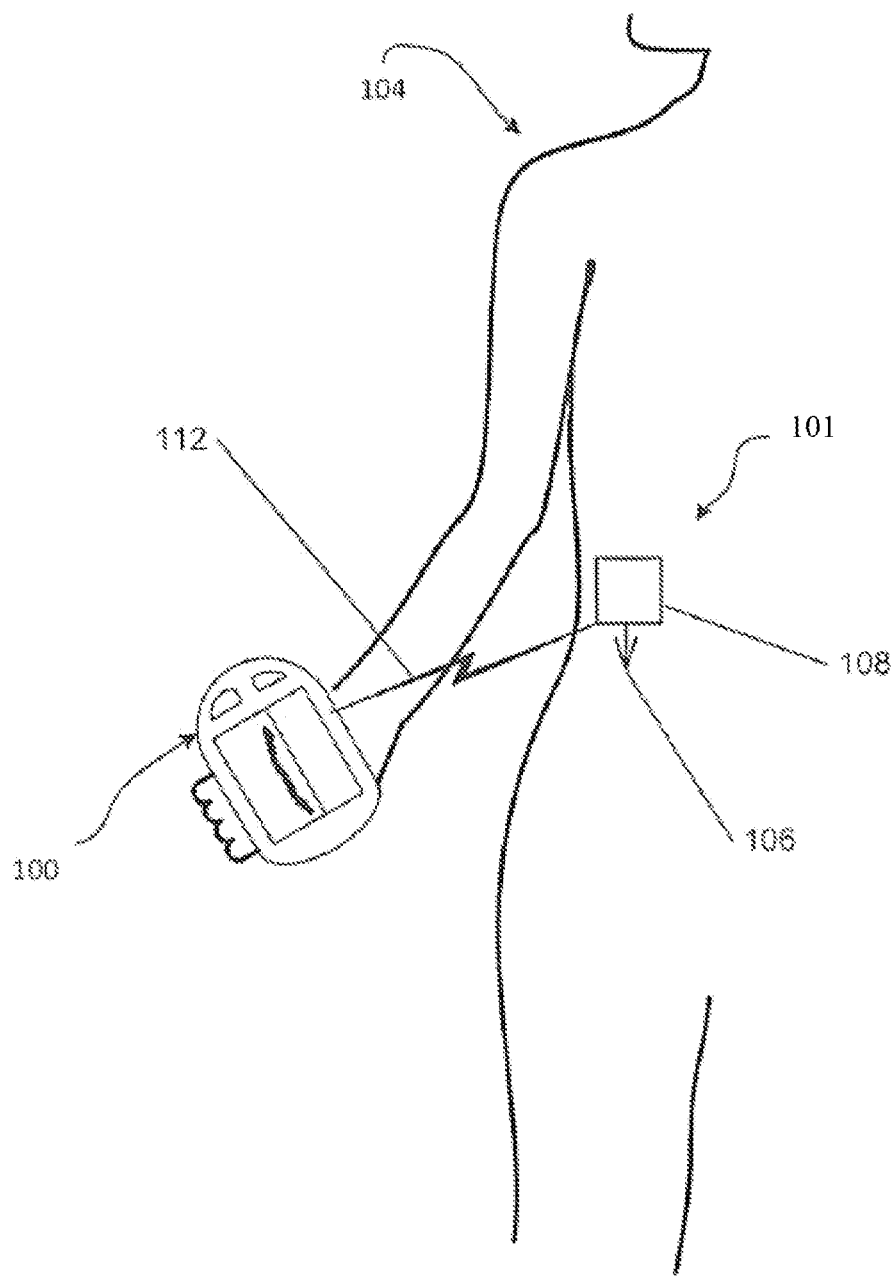
FIG. 4 is an embodiment of a CGM for use with embodiments of the disclosure.

FIG. 4 depicts an example CGM system that can be used in conjunction with one or more embodiments of the ambulatory infusion pump system of the present disclosure. The CGM system includes a sensor 101, a sensor probe 106, a sensor body 108, a receiver, and a monitor (receiver and monitor are depicted as device 100 in FIG. 4). The sensor 101 is removably affixed to a user 104 and includes a sensor probe 106 configured for transcutaneous insertion into the user 104. When placed, the sensor probe 106 reacts with the user's interstitial fluid which produces a signal that can be associated with the user's blood glucose level. The sensor 101 further includes a sensor body 108 that transmits data associated with the signal to the receiver 100 via wired or wireless connection (as represented by arrow line 112). In preferred embodiments, the receiver 100 receives the transmitted data wirelessly by any suitable means of wireless communication. By way of example only, this wireless communication may include a near field communication (NFC) radio frequency (RF) transmitter or a transmitter operating according to a "Wi-Fi" or Bluetooth® protocol, Bluetooth® low energy protocol or the like. Further detail regarding such systems and definitions of related terms can be found in, e.g., U.S. Pat. Nos. 8,311,749, 7,711,402 and 7,497,827, each of which is hereby incorporated by reference in its entirety.

With the infusion pump and CGM interfaced, the CGM can automatically transmit the CGM data to the pump. The pump can then use this data to automatically determine therapy parameters and suggest a therapy adjustment to the user or automatically deliver the therapy adjustment to the user. These therapy parameters including thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

For example, if the CGM readings indicate that the user has or is predicted to have a high blood glucose level (hyperglycemia), the ambulatory infusion system can automatically calculate an insulin dose sufficient to reduce the user's blood glucose level below a threshold level or to a target level and automatically deliver the dose. Alternatively, the ambulatory infusion system can automatically suggest a change in therapy upon receiving the CGM readings such as an increased insulin basal rate or delivery of a bolus, but can require the user to accept the suggested change prior to delivery rather than automatically delivering the therapy adjustments.

By way of further example, if the CGM readings indicate that the user has or is predicted to have a low blood glucose level (hypoglycemia), the ambulatory infusion system can, for example, automatically reduce or suspend a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the patient address the hypoglycemic condition as necessary (e.g., ingest carbohydrates), singly or in any desired combination or sequence. Such determination can be made by the infusion pump providing therapy or by a separate device that transmits therapy parameters to the infusion pump. In some embodiments, multiple medicaments can be employed in such an ambulatory infusion system as, for example, a first medicament, e.g., insulin, that lowers blood glucose levels and a second medicament, e.g., glucagon, that raises blood glucose levels.

As noted above, some closed loop or automated insulin delivery (AID) systems that automatically deliver at least some insulin based on data from a CGM can include a sleep mode that sets a more aggressive (i.e., lower and narrower) glucose target or target range when a user is sleeping. For example, in a system where the primary target range is 112.5 mg/dL to 160 mg/dL, the target range during sleep mode may be 110 mg/dL to 120 mg/dL. Due to the increased stability provided by the sleep mode target range, it is desirable to transition to the sleep mode target range as quickly as possible, while ensuring that the transition is done safely and does not risk low glucose or hypoglycemia by too quickly switching to the lower and narrower target range. Transitioning to sleep mode can increase this risk when, for example, there has been high CGM variability prior to sleep mode, the user has recently exercised or received a bolus, and when activities that can affect blood glucose that are not entered into or detected by the pump have occurred (e.g., exercise, sleep, menstrual cycle, meals). Such systems may further include additional modes with target ranges that vary from the default target range and/or modify the target range for other reasons. Systems and methods disclosed herein therefore provide various approaches for safely and quickly transitioning to sleep mode or other varied target ranges in order to improve time in range overnight by being more aggressive to get to the lower sleep mode or other target faster without unduly increasing the risk of hypoglycemia.

In embodiments, an AID system can utilize bolus information to determine the speed at which the system transitions to the sleep mode target or target range or other target/range. As noted above, sleep mode, for example, uses more aggressive targets because of the assumption that the user does not administer a bolus dose, exercise, or do any activities that increase the risk of hypoglycemia during sleep. Of the various risk factors, delivery of boluses is an activity that is known to increase this risk. The system can therefore transition to sleep mode or another target range based on a bolus look back period that determines a time since a most recent bolus.

In some embodiments, the predetermined time period can be based on an estimated insulin action time (IAT) used by the system, or the amount of time that insulin delivered to the user is estimated to remain active in the user's system. For example, in an embodiment the AID system can utilize an IAT of 5 hours. During sleep or other transition, if it is been more than 5 hours since the last bolus, sleep mode can quickly transition to the more aggressive target range, including immediately switching to the sleep mode range. If a bolus has been given in the last 5 hours, the transition can occur more slowly. For example, the applied target range can gradually move closer to the final sleep mode range over time, such as by moving an additional increment each hour, half-hour, etc. In embodiments, the time to fully transition to the sleep mode or other target range can be inversely proportional to the time since the last bolus.

The "last bolus" or "most recent bolus" used by the system for transitioning to sleep mode can in some embodiments only include user-initiated boluses (e.g., meal boluses) and not automatic correction boluses delivered by the closed loop algorithm. Alternatively, the "last bolus" can further include automatic correction boluses. In addition, in some embodiments boluses below a certain size can be disregarded. For example, if the user delivered a very small meal bolus below a low threshold level within the bolus look back period, the bolus can be disregarded because of the minimal effect the bolus would have on blood glucose. In some embodiments, rather than automatically exiting sleep mode based on a programmed sleep schedule or manually exiting by the user, the system can remain in sleep mode until a bolus is delivered.

Figure 5:
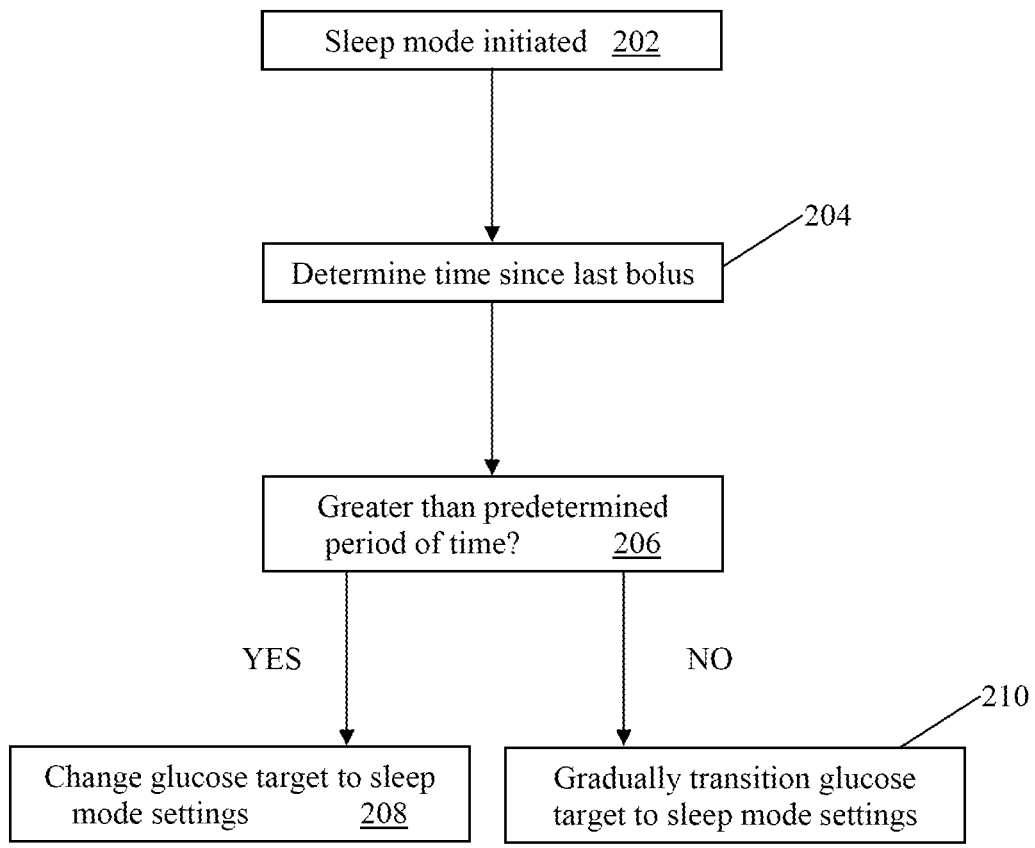
FIG. 5 is a flowchart of method steps for transitioning to a sleep mode in automated insulin delivery according to an embodiment of the disclosure.

Referring to FIG. 5, a flowchart of steps taken for transitioning to sleep mode according to an embodiment is depicted. At step 202, sleep mode is initiated. This can be done, for example, automatically by the system according to a predetermined sleep schedule or sleep mode can be manually initiated by the user. When sleep mode is initiated, at step 204 the system determines when the most recent bolus was delivered. As noted above, in some embodiments only manually delivered boluses such as meal boluses are reviewed for the most recent bolus rather than automatic correction boluses delivered by the system based on CGM data. At step 206 it is determined if the time since the most recent bolus is greater than a predetermined time period. The predetermined time period can be, for example, an insulin action time estimate used by the system to estimate the amount of time that insulin delivered to the user remains active in the user's body. If the amount of time since the most recent bolus is greater than the predetermined time period, the system can immediately or quickly transition to the lower and narrower glucose target or target range in sleep mode. If the predetermined period of time has not elapsed since the most recent bolus, the system can gradually transition to the sleep mode range, as discussed above. As noted above, such embodiments can also be applied to other modes with varying target ranges and/or any other circumstances when the system is transitioning to a different target range.

In embodiments, the transition to sleep mode or other modified target range can be determined algorithmically based on a probability of the user going below a low glucose threshold according to various factors. The factors can include patient-specific glucose level data and the probability of the user going low at a given time based on the data. For example, a mean glucose level and glucose variability can be tracked for a user based on time of day. Using such data retrospectively enables the system to determine a probability of the user going below the low glucose threshold for any given period of time (e.g., each hour, each half hour etc.) over the course of a day. A patient-specific sleep schedule can be set based on the glucose level data. Such a sleep schedule could immediately transition to the sleep mode target when activated or gradually transition based on the patient-specific glucose level data and the risk at a given time. Thus, rather than the user manually programming and or activating sleep mode, the user's sleep schedule can be automatically determined and set algorithmically from analysis of the user's glucose level data.

Figure 6:
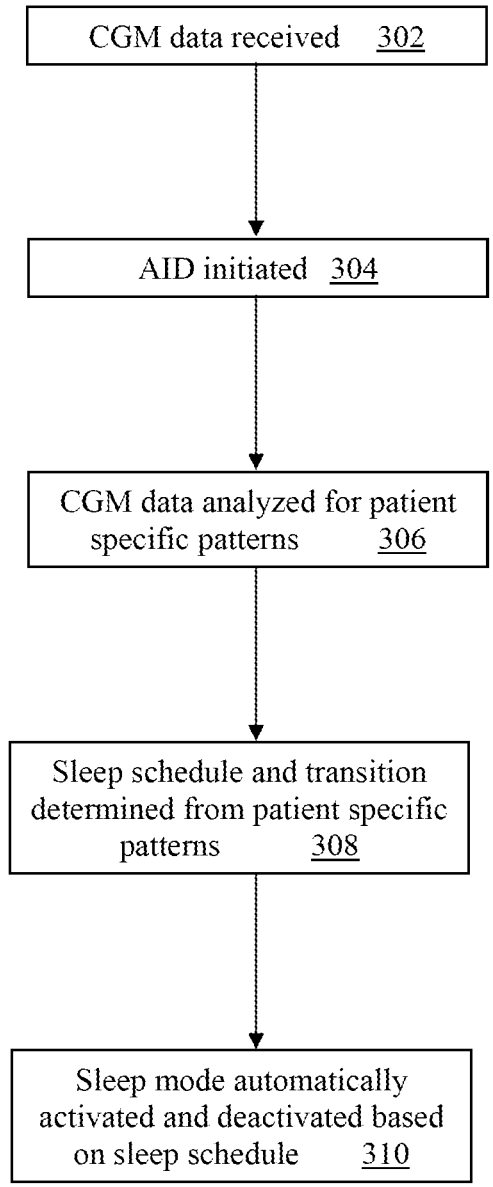
FIG. 6 is a flowchart of method steps for transitioning to a sleep mode in automated insulin delivery according to an embodiment of the disclosure.

Referring now to FIG. 6, a flowchart of steps taken for transitioning to sleep mode according to an embodiment is depicted. At step 302 the system is receiving CGM data and at step 304 automated insulin delivery using the CGM data is initiated. At step 306, the CGM data is analyzed for patient-specific patterns, such as, for example, for mean glucose level and glucose variability over a course of a day. The patient-specific glucose level patterns can be used to determine a sleep schedule for the user at step 308. At step 310, the system can automatically activate and deactivate sleep mode based on the sleep schedule determined from the user's glucose level data.

Such retrospective analysis of glucose level data can further be utilized to set various automated insulin delivery parameters throughout the day, including during sleep mode, based on the patient-specific risk profile created for the patient based on the glucose level data such as mean glucose level and variability throughout the day. For example, many AID systems include a safety factor that automatically reduces the size of automatic correction bolus to a predetermined amount, such as, for example, 60% of the calculated amount. In embodiments, the amount of the calculated automatic correction bolus that is delivered can vary based on the patient-specific profile, with a higher percentage being delivered at times when the user has more stable and/or higher glucose levels and a smaller percentage delivered when the user has more variable and/or lower glucose levels. Similarly, the glucose target and/or target range and the amount and frequency with which the system can modify the basal delivery of insulin can vary by time of day based on the risk profile, with the glucose targets being lower and the ability to modify the basal rate greater at times of lower risk.

In some embodiments, information other than glucose level data can be utilized to determine a user's risk profile and/or sleep schedule. For example, information obtained from smartphones, activity monitors, smartwatches, etc. could be used to account for behaviors, such as, for example, activity, in addition to the effect on glucose levels. Such activity information and other data can be utilized to further refine the user's sleep schedule and/or other treatment parameters. In addition, information from such devices can in some embodiments be used to automatically determine when a user is sleeping to initiate sleep mode on the pump. In embodiments, GPS location data and/or calendar events can be used as a proxy to determine activity level when direct activity data is unavailable.

In embodiments, the transition to sleep mode or other target range can be based on an estimated amount of insulin on board active in the user's body. As noted above, AID systems utilize a period of time, IAT, that insulin is estimated to remain active in the system, such as, for example, 5 hours. Therefore, utilizing the IAT estimate and the known history of insulin delivery the system, the system can estimate the user's IOB at any given time. The system can base its transition to the lower sleep mode or other target on this estimate of insulin on board because the more insulin that is active in the user's system, the greater the risk will drop below a low glucose threshold. Therefore, the system can delay or slow the transition until the estimated IOB for the user is below a predetermined threshold level. In some embodiments, the system will not transition to the lower target until the estimated IOB is below the predetermined threshold. In various embodiments, the predetermined threshold can be zero units or a non-zero amount, can be a patient-specific setting based on, e.g., the correction factor for the user, etc. In other embodiments, the system can gradually transition to the lower target if the estimated IOB is above the threshold and can transition at a speed inversely proportional to how far above the threshold such that the closer the estimated IOB is to the threshold, the more quickly the system transitions to the lower range.

Figure 7:
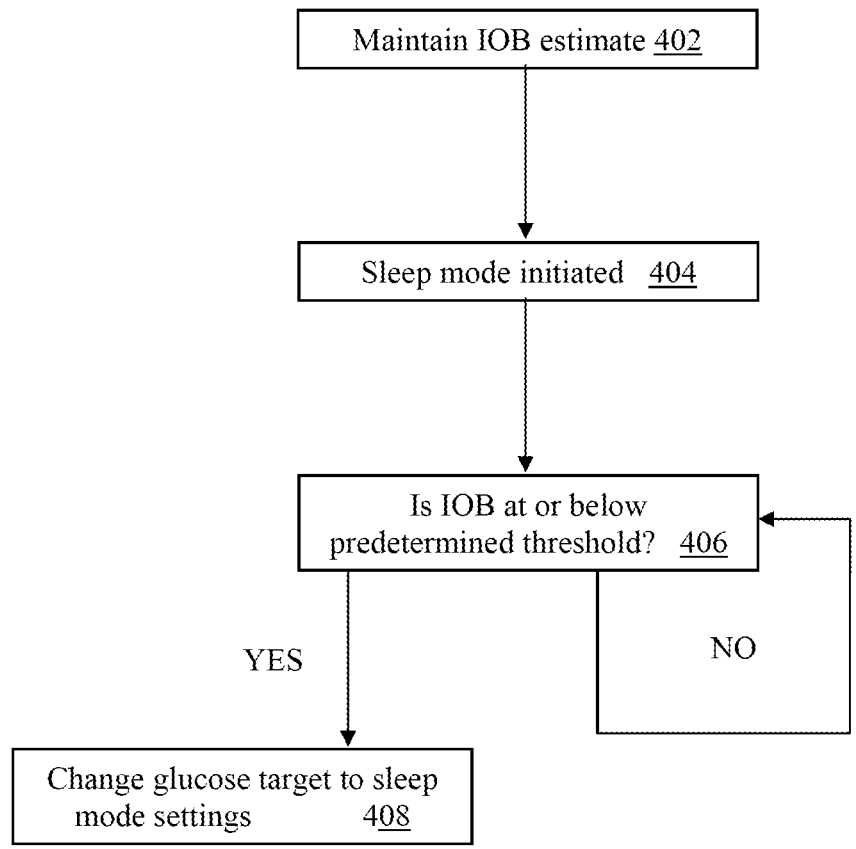
FIG. 7 is a flowchart of method steps for transitioning to a sleep mode in automated insulin delivery according to an embodiment of the disclosure.

Referring now to FIG. 7, a flowchart of steps taken for transitioning to sleep mode according to an embodiment is depicted. At step 402 an estimate of the amount of insulin on board in the user is maintained. When sleep mode is initiated at step 404, it is determined at step 406 if the estimated IOB is below at or below a predetermined threshold (e.g., zero units). If the estimated IOB is at or below the threshold, at step 408 the system can immediately change the glucose target to the sleep mode settings. If the estimated IOB is not at or below the threshold, the system can prevent the transition to the sleep mode range until below the threshold by continuously and/or regularly comparing the current estimate IOB to the predetermined threshold. Once the estimate IOB is at or below the threshold, the system can then transition to the sleep mode settings. As noted above, such embodiments can also be applied to other modes with varying target ranges and/or any other circumstances when the system is transitioning to a different target range.

Although the sleep mode or other transition to a new target mode discussed herein is primarily described as increasing aggressiveness by lowering and/or narrowing a target glucose level or target range, the AID algorithm can increase aggressiveness in any number of additional or alternative ways. For example, the system can increase aggressiveness by lowering thresholds for determining adjustments to basal delivery, increasing a maximum amount by which basal delivery can be modified, decreasing an estimate of insulin action time, etc.

Various other factors can also aid in determining when and how quickly to transition to a sleep mode or other mode or target range. Such factors can include, for example, how far a patient's glucose level is from a target or target range when, e.g., sleep mode is initiated or during sleep mode, whether the patient is above or below the target, and how long the patient has been in sleep mode. The system also may not transition as quickly if it determines that certain user settings are incorrect or not optimal, such as open loop settings applied as a default when automated delivery is exited. Further factors that can affect transition aggressiveness include illness, compression loss at the CGM sensor, quality of CGM sensor, sensor end of life, sensor signal noise, use of acetaminophen, use of different insulin types, recent infusion set change or end of life, use of other insulin delivery mechanisms, e.g., inhalable or injection, leading to unknown IOB, travel/time zone changes, sleep deprivation, recent high and low glucose levels, recent glucose variability/oscillations, predicted glucose highs and lows, changes in behavior such as diet and exercise increase or decrease, recent childbirth, patient age and patient weight.

In addition, although referred to herein as sleep mode and primarily applied to when a user is sleeping, sleep mode could also be used when a user is entering or maintaining an extended period of rest and/or inactivity. Similarly, the concepts described above can be used for other transitions, such as, for example, transitioning to new target range. For example, any time the system transitions to a lower target range, whether for sleep mode or other reason(s), one or more of the transition features described above could be employed. In addition, such transitions can be employed in certain embodiments when the target range is raised.

In another embodiment, the system can transition to the sleep mode or other modified targets linearly from the previous targets over a period of time following activation of sleep or other mode, such as, for example, 3 hours.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated. With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; 10,569,016; 10,736,037; 10,888,655; and 10,994,077. commonly owned U.S. Patent Publication Nos. 2009/0287180; 2012/0123230; 2013/0053816; 2014/0276423; 2014/0276569; 2014/0276570; 2018/0071454; 2019/0240398; 2019/0307952; 2019/0365997; 2020/0114076; 2020/0206420; 2020/0261649; 2020/0306445; 2020/0329433; 2020/0368430; 2020/0372995; 2021/0001044; 2021/0113766; and 2021/0154405 and commonly owned U.S. patent application Ser. Nos. 17/323,529 and 17/368,968.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion pump system, comprising:
a pump mechanism configured to facilitate delivery of insulin to a user;
a communications interface adapted to receive glucose levels from a continuous glucose monitor;
at least one processor functionally linked to the pump mechanism and the communications interface, the at least one processor configured to:
automatically calculate insulin doses with a closed loop delivery algorithm based on glucose levels received from the continuous glucose monitor, the closed loop delivery algorithm configured to calculate the insulin doses to maintain a user's glucose levels within a first target glucose range including a low glucose threshold and a high glucose threshold;
automatically deliver the insulin doses calculated by the closed loop delivery algorithm to the user with the pump mechanism;
determine that the first target glucose range should be modified from the first target glucose range to a second target glucose range;
determine an amount of time elapsed since a most recent bolus delivery of insulin has been delivered by the pump mechanism;
immediately transition from the first target glucose range to the second target glucose range if the amount of time since the most recent bolus delivery of insulin is greater than a predetermined amount of time from the determination to modify the first target glucose range; and
gradually transition from the first target glucose range to the second target glucose range if the amount of time since the most recent bolus delivery of insulin is less than the predetermined amount of time from the determination to modify the first target glucose range.

2. The ambulatory infusion pump system of claim 1, where the at least one processor is configured to determine the most recent bolus delivery of insulin based only on meal boluses manually programmed by the user.

3. The ambulatory infusion pump system of claim 1, wherein the at least one processor is configured to determine the most recent bolus delivery of insulin based on meal boluses manually programmed by the user and automatic correction boluses calculated by the closed loop delivery algorithm.

4. The ambulatory infusion pump system of claim 1, wherein the second target glucose range has a lower low glucose threshold and a lower high glucose threshold than the first glucose target range.

5. The ambulatory infusion pump system of claim 4, wherein the second target glucose range is activated as part of a sleep mode configured to be operated when the user is sleeping.

6. The ambulatory infusion pump system of claim 1, wherein the at least one processor is configured to automatically determine that the first target glucose range should be modified from the first target glucose range to the second glucose target range.

7. The ambulatory infusion pump system of claim 6, wherein the at least one processor is configured to automatically determine that the first target glucose range should be modified based on a preprogrammed schedule.

8. The ambulatory infusion pump system of claim 7, wherein the at least one processor is configured to determine that the first target glucose range should be modified based on a preprogrammed schedule by receiving user input instructing the processor to modify the first target glucose range at a predetermined time.

9. The ambulatory infusion pump system of claim 1, wherein the at least one processor is configured to gradually transition from the first target glucose range to the second target glucose range such that a time to fully transition to the second target range is inversely proportional to the amount of time that elapsed since the most recent bolus.

10. The ambulatory infusion pump system of claim 1, where in the predetermined amount of time is determined based on an estimated insulin action time used by the closed loop delivery algorithm.

11. An ambulatory infusion pump system, comprising:
a pump mechanism configured to facilitate delivery of insulin to a user;
a communications interface adapted to receive glucose levels from a continuous glucose monitor;
at least one processor functionally linked to the pump mechanism and the communications interface, the at least one processor configured to:
automatically calculate insulin doses with a closed loop delivery algorithm based on glucose levels received from the continuous glucose monitor, the closed loop delivery algorithm configured to calculate the insulin doses to maintain a user's glucose levels within a first target glucose range including a low glucose threshold and a high glucose threshold;
automatically deliver the insulin doses calculated by the closed loop delivery algorithm to the user with the pump mechanism;
determine that the first target glucose range should be modified from the first target glucose range to a second target glucose range;
determine an amount of time elapsed since a most recent bolus delivery of insulin has been delivered by the pump mechanism;
alter the first target glucose range to the second target glucose range if the amount of time since the most recent bolus delivery of insulin is greater than a predetermined amount of time from the determination to modify the first target glucose range.

12. The ambulatory infusion pump system of claim 11, wherein if the most recent bolus delivery of insulin was less than the predetermined amount of time from the determination to modify the first target glucose range the at least one processor is configured to gradually transition from the first target glucose range to the second target glucose range.

13. The ambulatory infusion pump system of claim 12, wherein the at least one processor is configured to gradually transition from the first target glucose range to the second target glucose range such that a time to fully transition to the second target range is inversely proportional to the amount of time that elapsed since the most recent bolus.

14. The ambulatory infusion pump system of claim 11, where the at least one processor is configured to determine the most recent bolus delivery of insulin based only on meal boluses manually programmed by the user.

15. The ambulatory infusion pump system of claim 11, wherein the at least one processor is configured to determine the most recent bolus delivery of insulin based on meal boluses manually programmed by the user and automatic correction boluses calculated by the closed loop delivery algorithm.

16. The ambulatory infusion pump system of claim 11, wherein the second target glucose range has a lower low glucose threshold and a lower high glucose threshold than the first glucose target range.

17. The ambulatory infusion pump system of claim 16, wherein the second target glucose range is activated as part of a sleep mode configured to be operated when the user is sleeping.

18. The ambulatory infusion pump system of claim 11, wherein the at least one processor is configured to automatically determine that the first target glucose range should be modified from the first target glucose range to the second glucose target range.

19. The ambulatory infusion pump system of claim 18, wherein the at least one processor is configured to automatically determine that the first target glucose range should be modified based on a preprogrammed schedule.

20. The ambulatory infusion pump system of claim 11, wherein the predetermined amount of time is determined based on an estimated insulin action time used by the closed loop delivery algorithm.

* * * * *